(12) United States Patent
Ji et al.

(10) Patent No.: US 9,437,638 B2
(45) Date of Patent: Sep. 6, 2016

(54) PHOTODETECTOR FOR IMAGING SYSTEM

(75) Inventors: Fan Ji, Kirkkonummi (FI); Mikko Juntunen, Kirkkonummi (FI); Iiro Hietanen, Harkapaa (FI)

(73) Assignee: Detection Technology Oy, Micropolis, FIN-91100 (FI)

( * ) Notice: Subject to any disclaimer, the term of this patent is extended or adjusted under 35 U.S.C. 154(b) by 576 days.

(21) Appl. No.: 12/602,954

(22) PCT Filed: Jun. 4, 2008

(86) PCT No.: PCT/EP2008/056933
§ 371 (c)(1),
(2), (4) Date: Apr. 6, 2010

(87) PCT Pub. No.: WO2008/148815
PCT Pub. Date: Dec. 11, 2008

(65) Prior Publication Data
US 2010/0200940 A1    Aug. 12, 2010

(30) Foreign Application Priority Data
Jun. 4, 2007   (GB) .................................. 0710629.7

(51) Int. Cl.
*H01L 27/146* (2006.01)
*H01L 21/768* (2006.01)

(52) U.S. Cl.
CPC ... *H01L 27/14634* (2013.01); *H01L 21/76898* (2013.01); *H01L 27/14658* (2013.01); *H01L 2924/0002* (2013.01)

(58) Field of Classification Search
None
See application file for complete search history.

(56) References Cited

U.S. PATENT DOCUMENTS

| | | | | |
|---|---|---|---|---|
| 5,998,292 | A | * 12/1999 | Black et al. | 438/618 |
| 6,175,141 | B1 | * 1/2001 | Hofbauer et al. | 257/444 |
| 6,265,308 | B1 | 7/2001 | Bronner et al. | |
| 7,057,254 | B2 | 6/2006 | Bui et al. | |
| 8,102,057 | B2 | * 1/2012 | Leon et al. | 257/774 |
| 2004/0129992 | A1 | 7/2004 | Shibayama | |
| 2004/0222482 | A1 | 11/2004 | Bui et al. | |
| 2004/0261839 | A1 | * 12/2004 | Gee et al. | 136/256 |
| 2004/0263839 | A1 | 12/2004 | Diehr et al. | |

(Continued)

FOREIGN PATENT DOCUMENTS

| | | |
|---|---|---|
| CN | 1244949 A | 2/2000 |
| CN | 1685513 A | 10/2005 |

(Continued)

OTHER PUBLICATIONS

GB0710639.7 Examination Report, Apr. 27, 2011.*

(Continued)

*Primary Examiner* — Andres Munoz
(74) *Attorney, Agent, or Firm* — Ryan, Mason & Lewis, LLP (57) ABSTRACT

There is disclosed a substrate including at least one photodetector, the photodetector having a first active area on a first surface of the substrate and a second active area on a second surface of the substrate, wherein the photodetector is provided with a conductive via electrically isolated from the substrate, said conductive via extending through the photodetector from the first surface of the substrate to the second surface of the substrate for connecting the first active area to the second surface of the substrate, the second surface providing electrical connections for the first and second active areas of the photodetector.

14 Claims, 10 Drawing Sheets

(56) References Cited

U.S. PATENT DOCUMENTS

| | | |
|---|---|---|
| 2005/0098855 A1 | 5/2005 | Shimoji et al. |
| 2006/0046471 A1 | 3/2006 | Kirby et al. |
| 2006/0097290 A1* | 5/2006 | Hietanen ................. 257/233 |
| 2006/0121690 A1* | 6/2006 | Pogge et al. ............. 438/455 |
| 2006/0231961 A1 | 10/2006 | Shibayama et al. |
| 2008/0067622 A1* | 3/2008 | Bui et al. ................. 257/458 |
| 2008/0099870 A1* | 5/2008 | Wilson et al. ............ 257/446 |

FOREIGN PATENT DOCUMENTS

| | | |
|---|---|---|
| CN | 1708840 A | 12/2005 |
| CN | 200880101916.9 | 3/2014 |
| CN | 2008801019169 | 8/2014 |
| GB | 2392307 A | 2/2004 |
| WO | WO03/083944 A1 | 10/2003 |
| WO | WO2004/012274 A1 | 2/2004 |
| WO | WO2007/023416 A1 | 3/2007 |

OTHER PUBLICATIONS

GB1119260.6 Examination Report, Nov. 30, 2011.*
Search Report for PCT/EP2008/056933 dated Oct. 22, 2008.
Search Report for GB0710629.7 dated Sep. 20, 2007.

* cited by examiner

PHOTODETECTOR FOR IMAGING SYSTEM

The present application claims priority to the international patent application identified as PCT/EP2008/056933 filed on Jun. 4, 2008, which itself claims priority to the UK patent application identified as GB 0710629.7 filed on Jun. 4, 2007, the disclosures of which are both incorporated herein by reference in their entirety.

FIELD OF THE INVENTION

The present invention relates to semiconductor devices having active areas formed on both sides of a substrate, and particularly but not exclusively to photo-detectors for use in imaging systems.

BACKGROUND OF THE INVENTION

Photo-detectors are used in imaging systems for medical, security and industrial applications. One particular medical application of photo-detectors is in computed tomography (CT) systems.

In a typical CT system, an X-ray source with a fan-shaped X-ray beam and a two-dimensional radiation detector array are assembled on a mechanical support structure, known as a gantry. In use, the gantry is rotated around an object to be imaged in order to collect X-ray attenuation data from a constantly changing angle with respect to the object. The plane of the gantry rotation is known as an imaging plane, and it is typically defined to be the x-y plane of the coordinate system in a CT system. In addition, the gantry (or more typically the object) is moved slowly along the z-axis of the system in order to collect x-ray attenuation data for a required length of the object. Examples of CT systems are discussed in U.S. Pat. Nos. 6,144,718 and 6,173,031.

The radiation detectors of current state of the art CT systems consist of a two-dimensional array of rare earth metal based scintillators and a corresponding two-dimensional array of silicon photodiodes. Both the scintillator crystals and the photodiodes are manufactured in two-dimensional arrays, which are then optically coupled to one another during detector manufacturing.

Figure 1:
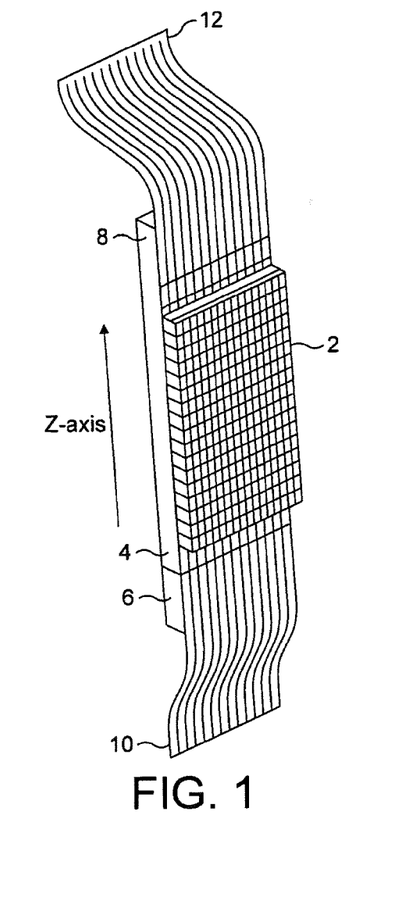
FIG. 1 illustrates the basic construction of a photodetector array in accordance with one known arrangement.

A typical detector array is shown in FIG. 1. A typical detector consists of an array of 16 rows and 16 columns of individual detector elements, i.e. 256 elements in total. Columns are organised in the z direction. The construction of the detector is well-known in the art. The array of detectors is generally illustrated in FIG. 1 by reference numeral 2. The z direction or z-axis is also shown in FIG. 1. The elements in rows are in the imaging plane, and produce sets of data known as 'slices'. In a medical CT machine, for example, each slice image corresponds to a two-dimensional X-ray image of a thin slice of a human body as seen in the direction of the body axis and the machine z-axis.

In CT imaging systems, the size of the detector in the imaging plane is increased by placing individual detector arrays, such as the array shown in FIG. 1, adjacent to each other to thereby increase the size of the detector in the imaging plane. An edge 4 of the detector of FIG. 1 may be placed alongside a corresponding edge of a corresponding detector array, and thereby a larger area can be built up.

A key trend in the CT industry is to build CT machines with more detector elements in order to collect more X-ray attenuation data for each gantry rotation and therefore to speed up the measurements, to improve the accuracy of the measurements, and to decrease patient radiation dose in medical applications. An increase in the number of detector elements similarly may have advantages in other imaging applications, and is not restricted to medical or CT systems.

In CT detector constructions, a major limiting factor in providing more detector elements is the need to readout the electrical signals from the individual photo-detectors of the detector array. In the current art, the readout of these signals is facilitated by manufacturing very narrow metal lines (typically 5 to 20 µm) on top of the photo-detector chip, between the active photo-detector elements. A single metal line carries the signal of one photo-detector to the edge of the photo-detector chip, in the z direction, to an area which is specially reserved for the purpose of connecting the signals from the photo-detectors by wire bonding to a substrate placed beneath the photo-detector chip or to a multiplexing or signal processing ASIC chip. Using this method, there is a physical limitation on the size of a photo-detector array that may be manufactured. The number of electrical elements at the chip edge is limited, and this limits the number of photo-detector elements which can be connected. The detector cannot get larger in the z-direction in particular.

This is illustrated by FIG. 1. The photo-detector array 2 is provided with an area 6 and 8 either side of the array in the z direction, which areas provide for connection to a respective set of electrical wires, 10 and 12. The signals from the photo-detector array may be multiplexed or processed in integrated electronics chips or ASICs located in areas 6 and 8 before the signals are connected to electrical wires, 10 and 12. Because of the need to accommodate the physical wires and their connections, the number of photo-detectors in an array is limited. In particular, it is not possible to add further photo-detectors in the z direction. The physical wires 10 and 12 prevent any expansion of the photo-detector array in the z direction, such that additional photo-detector arrays cannot be added in the z direction. That is, although photo-detectors can be joined together side-by-side, in the horizontal direction in FIG. 1, they cannot be joined top-to-bottom, in the vertical direction. This is because of the need to connect the wires 10 and 12 at the top and bottom.

A photo-detector with the possibility of expansion in the z direction is known as a 'tileable' detector. In order to provide a tileable detector, it is necessary to make the electrical connections to each photo-detector without wiring the photodetectors to the photo-detector chip edge. If this can be achieved, there is no limit to the growth of the photo-detector array and consequently the number of photo-detector elements.

One solution to the problem of achieving a tileable detector is suggested in European Patent No. 1525623 in the name of Detection Technology. This document discloses a technique in which the connections for the anode and cathode of a photodiode device are provided on a single side of a substrate. This is achieved by forming a conductive via through the substrate and adjacent the photodetector device, for contacting an active area on one surface of the substrate to the other surface of the substrate.

Embodiments of the present invention aim to address one or more of the above problems and to provide an improved photodetector array.

SUMMARY OF THE INVENTION

The invention provides a method of forming a via in at least one layer of a semiconductor device, comprising the steps: partially etching the at least one layer to form a first opening, of a first width, therein; and etching the at least one layer to form a second opening, of a second width smaller than said first width, through the at least one layer, wherein the via is formed of the first and second openings.

The step of etching may be performed after the step of partial etching, the step of etching comprising etching a portion of the at least one layer not removed by the partial etching step.

The step of etching may be performed at the underside of the semiconductor device, such that the via is formed with the first width at the underside, and with the second width at the other side of the at least one layer.

The at least one layer may be a layer of a photodetector device.

The at least one layer may include a substrate.

The at least one layer may include an implant layer formed on the underside of the substrate.

The at least one layer may include a silicon dioxide layer formed on the underside of the implant layer.

A protective low temperature oxide layer may be formed on the underside of the silicon dioxide layer.

A photoresist layer may be formed on the underside of the protective low temperature oxide layer.

An opening may be formed in the photoresist layer, prior to etching, of the first width.

The step of partially etching the at least one layer may comprise etching through the protective low temperature oxide layer, the silicon dioxide layer, and the implant layer, and partially etching into the substrate.

A further photoresist may be formed on the underside of the at least one layer and in the formed opening.

The further photoresist may be patterned to form an opening of the second width.

The step of etching the at least one layer to form a second opening may comprise etching through the substrate.

There may be formed, on the upper surface of the substrate, an implant layer, a field oxide layer or the implant layer, and a photoresist layer on the field oxide layer.

The step of etching may further comprise etching the implant layer and field oxide layer.

The method may further comprise forming a layer of silicon oxide on the sidewalls of the formed via.

The method may further comprise filling the via with polysilicon.

The invention also provides a semiconductor device having a via formed in at least one layer thereof, the via comprising: a first portion of a first width extending partially through said at least one layer; and a second portion of a second width, smaller than said first width, extending through the remainder of the at least one layer.

The semiconductor device may comprise a photodetector.

The via may be filled with polysilicon.

The via may have silicon dioxide formed on sidewalls thereof.

The device further comprises a first implant layer formed at an upper surface of the at least one layer, and a second implant layer formed at the underside of the at least one layer.

The semiconductor device may further comprise a conductive layer at the upper surface for connecting the polysilicon in the via to the implant layer at the first surface, and a conductive layer at the underside for connecting the polysilicon to a further connection.

The semiconductor may further comprise a further conductive layer at the underside for connecting the implant layer at the underside to a further connection.

The conductive layer and further conductive layer may comprise contact pads for the implant layer at, respectively, the upper surface and underside of the at least one layer.

The invention provides a substrate including at least one photodetector, the photodetector having a first active area on a first surface of the substrate and a second active area on a second surface of the substrate, wherein the photodetector is provided with a conductive via electrically isolated from the substrate, said conductive via extending through the photodetector from the first surface of the substrate to the second surface of the substrate for connecting the first active area to the second surface of the substrate, the second surface providing electrical connections for the first and second active areas of the photodetector.

The photodetector is a photodetector device. The first and second surface are on opposite sides of the substrate.

The invention also provides a photodetector including a substrate, the photodetector having a first active area on a first surface of the substrate and a second active area on a second surface of the substrate, wherein the photodetector is provided with a conductive via electrically isolated from the substrate, said conductive via extending through the photodetector from the first surface of the substrate to the second surface of the substrate for connecting the first active area to the second surface of the substrate, the second surface providing electrical connections for the first and second active areas of the photodetector.

Said conductive preferably via extends through the first active area.

Said conductive via is preferably electrically isolated from the substrate. Said conductive via preferably comprises polysilicon. The polysilicon preferably fills the conductive via.

There is preferably provided a further conductive element on the second side of the substrate connected to the conductive via. The further conductive element on the second side of the substrate is preferably for making an off-chip connection to the first active area via the conductive via. The further conductive element is preferably an aluminium contact element.

There is preferably provided a further conductive element on the second side of the substrate connected to the second active area. The further conductive element on the second side of the substrate is preferably for making an off-chip connection to the second active area. The further conductive element is preferably an aluminium contact element.

The first active area is preferably an anode. The second active area is preferably a cathode.

There may be provided a plurality of photodetectors and a respective plurality of conductive vias for connecting a respective plurality of first active areas on the first surface of the substrate to the second surface of the substrate. The plurality of photodetectors are preferably formed as an array.

The photodetectors are preferably photodiodes. The photodetector is preferably a photodiode of a medical imaging system. The medical imaging system is preferably a computed tomography system.

The invention provides a substrate including a plurality of photodetectors, each photodetector of the plurality having an active area on a first surface of the substrate and a further active area on the second surface of the substrate, wherein each photodetector of the plurality is provided with a conductive via electrically isolated from the substrate, said via extending through the photodetector from the first surface of the substrate to the second surface of the substrate for connecting the active area to the second surface of the substrate, the second surface providing electrical connections for the first and second active areas of the plurality of photodetectors.

A photo-detector array including a plurality of sub-arrays of photo-detectors preferably includes such a substrate, wherein the plurality of said sub-arrays of photo-detectors are placed adjacent to each other in a matrix to form the photo-detector array.

The matrix preferably extends in two directions.

An imaging system preferably comprises: a radiation detector including a photo detector array as defined, a radiation source facing the radiation detector, and means for controlling the radiation detector and the radiation source.

The radiation source may be an X-ray tube equipped with a high-voltage generator.

The radiation detector and the radiation source may be radially mounted in a cylindrical scanning structure.

The means for controlling may comprise a computer system.

The invention provides a method of manufacturing a photodetector device comprising: forming a first active area of the photodetector device on a first surface of a substrate; forming a second active area on the second surface of the substrate; forming a conductive via electrically isolated from the substrate through the photodetector device from the first surface of the substrate to the second surface of the substrate; and connecting the first active area to the conductive via such that the first active area is connected to the second surface of the substrate.

The conductive via is preferably formed to extend through the first active area.

The method may further comprise the step of electrically isolating the conductive via from the substrate.

The method may further comprise the step of providing a further conductive element connected between the first active area of the device and the conductive via.

The method may further comprise the step of providing a further conductive element on the second side of the substrate connected to the conductive via. The further conductive element may be a contact pad. The further conductive element on the second side of the substrate is preferably provided for making an off-chip connection to the first active area via the conductive via.

The method may further comprise the step of providing a further conductive element on the second side of the substrate connected to the second active area. The further conductive element on the second side of the substrate is preferably provided for making an off-chip connection to the second active area.

The photodetector may be a photodiode. The first active area may be an anode and the second active area may be a cathode.

The method may further comprise the step of providing a plurality of photodetector devices and a respective plurality of conductive vias for connecting the active areas of the photodetector devices on the first surface of the substrate to the second surface of the substrate.

The invention provides a method of manufacturing a plurality of photodetector devices comprising: forming a plurality of first active area of the photodetector device on a first surface of a substrate; forming a corresponding plurality of second active area on the second surface of the substrate; forming a conductive via for each photodetector electrically isolated from the substrate through the photodetector device from the first surface of the substrate to the second surface of the substrate; and connecting the first active areas to the respective conductive vias such that the first active areas re connected to the second surface of the substrate.

BRIEF DESCRIPTION OF DRAWINGS

For better understanding of the present invention, and to show as to how the same may be carried into effect, reference will now be made by way of example to the accompanying drawings in which.

DESCRIPTION OF PREFERRED
EMBODIMENTS OF THE INVENTION

The present invention is described hereinafter with reference to a particular set of embodiments. However the invention is not limited to such embodiments.

The invention is particularly described herein with reference to an example of a photodetector array for a CT medical imaging system. The invention, and embodiments thereof, are however not limited to such applications.

Whilst the invention is illustrated herein by way of reference to various figures, none of these figures are drawn to scale, but rather are drawn to best illustrate various features of the present invention.

With reference to FIGS. 2(a) to 2(n), there are illustrated selected steps for manufacturing a photo-detector array for a CT imaging system in accordance with a preferred embodiment of the invention. A cross-section through an exemplary device substrate is used for the purpose of explaining the present invention. Only those steps relevant to an understanding of the present invention are shown. Other steps will be familiar to one skilled in the art. One skilled in the art will also be familiar with alternatives to certain steps presented herein in order to achieve the final structure in accordance with the invention.

Referring to FIG. 2(a) there is illustrated a cross-section of a n-type semiconductor substrate 30 in which a photo-detector element is formed. A p+ type implant layer 32 is formed in the upper surface of the substrate for forming an active area of a photo-diode. The active area 32 provides the anode of the photo-diode. A field oxide (FOX) layer 38 covers the upper surface of the substrate 30 above the p+ type layer 32.

An n+ implant layer 40 is formed in the under surface of the substrate 30, for forming the cathode of the photo-diode. A thin silicon dioxide layer 42 covers the underside of the substrate 30 and the n+ layer 40.

The structure of FIG. 2(a) may be fabricated using key process steps for manufacturing high quality diodes on silicon. Such standard techniques are known generally in the art, and especially in the art of fabricating photo-diodes for CT imaging applications, and are therefore not described herein. Process steps to achieve the structure shown in FIG. 2(a) are well-known.

After the fabrication of the structure illustrated in FIG. 2(a), a protective low temperature oxide (LTO) layer 44 is grown on the underside of the substrate, on the silicon dioxide layer 42 covering the n+ (cathode) region, as shown in FIG. 2(b).

A photo-resist layer 47, or other alternative protective layer, is then deposited on the upperside of the substrate 30, on the field oxide layer 32, to protect the upperside of the substrate during subsequent processing steps, as shown in FIG. 2(c).

In a standard lithographic patterning step, a photo-resist layer 46 is deposited on the underside of the substrate 30, on the low temperature oxide layer 44, as illustrated in FIG. 2(d). The photo-resist layer 46 is then patterned to form an opening (not shown) which is used as a mask for chemical etching of the low temperature oxide layer 44 and the thin oxide layer 42 on the underside of the substrate. In addition the mask is used to etch through the n+ type region 40 and partially into the substrate 30.

The resulting structure is illustrated in FIG. 2(e). The width of the hole is defined as x, corresponding to the width of the opening in the photo-resist formed for the etch process. The thus formed hole is denoted by reference numeral 45.

A further photo-resist layer 51 is then deposited on the underside of the substrate 30 to fill the opening 45. The photo-resist layer is then patterned to form an opening smaller than the width of the opening 45, such that the opening 45 has photo-resist sidewalls. As denoted by FIG. 2(f), the opening thus formed in the photo-resist layer 51 is denoted by a width y.

An inductively coupled plasma (ICP) reactor is then used for an etch of a high aspect ratio hole through the silicon wafer of the substrate 30 all the way through to the field oxide layer 38 to form a narrower opening 49, as shown in FIG. 2(g).

The photo-resist layer 51 is then removed from the underside of the substrate. The remaining low temperature oxide layer 44 and the thin oxide layer 42 are then also removed from the underside of the substrate by etching, as well as the portion of the field oxide layer 38 exposed in the opening 49. The resulting structure is illustrated in FIG. 2(h).

The foregoing paragraphs, referring to FIGS. 2(e) to 2(h), describe a preferred technique, in the context of forming an advantageous photodetector structure, of forming a via in a layer of a semiconductor device. One skilled in the art will appreciate that the via formation is not limited to the specifics of the photodetector structure. Thus the formation of the via is not dependent on the specific layers formed on the upper side or the underside of the substrate. The technique for forming the via is not limited to forming a via in a substrate; it may be used for forming a via in one or more layers of any semiconductor device. Still further, the disclosed techniques for forming the via are exemplary only; techniques other than the specifically disclosed photoresist and etching arrangements may be used.

The via formation is disclosed in a sequence of forming the wide opening with a partial etch, and then forming the narrow opening with an etch through the remaining material. However this sequence is not essential. In an alternative, for example, an initial etch step may form a narrow opening through the substrate from surface-to-surface. A subsequent etch may then form the wide opening partially through the substrate. That is, the etch sequence may be inverted from that described.

The preferred technique is, in general, to form a via through at least one layer, which via has a first portion and a second portion with different widths. In this way, the via may be considered "stepped". The via is also preferably formed such that the wider of the two portions is formed at the underside.

Typically the process of making the high aspect ratio holes or openings is a deep reactive ion etch (DRIE), also known as coupled plasma etching (ICP). It is a common characteristic of known etching processes that the holes are not perfectly perpendicular to the wafer surface. In practice, this means that if the hole position is defined on the top surface, by an opening on an oxide for example, and the etching is performed from that surface, the hole will appear on the back side at a different surface location. When the contact is then formed to connect to the via plug, after oxide insulation and conductive filling, it is not in the position it was expected to be. Thus the contact may be formed connecting only with the edge of the via, causing a short to the bulk substrate.

Figure 6:
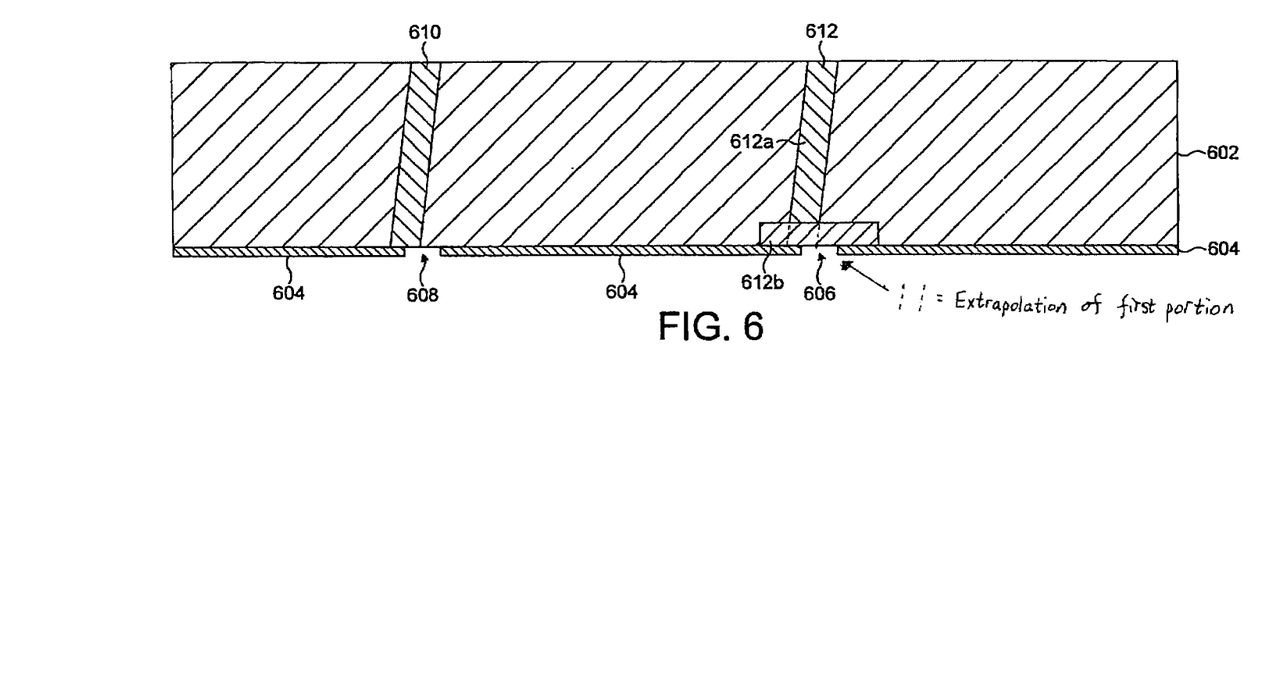
FIG. 6 illustrates an application of an advantageous inventive structure in accordance with an inventive arrangement.

This problem, and the advantage afforded by the inventive arrangement, can be understood with reference to FIG. 6. FIG. 6 shows an exemplary substrate 602. Two vias are formed through the substrate 602, denoted by reference numerals 610 and 612. An oxide layer 604 is formed on the underside of the substrate, having openings 608 and 606 for allowing connection to, respectively, the material formed in the vias 610 and 612.

The via 610 is formed in accordance with prior art techniques, and is a high aspect ratio via. As discussed above, the via is not formed perpendicular to the surface of the substrate, and thus the via opening at one surface is not correctly aligned with the via opening at the other surface. As can be seen in FIG. 6, the opening 608 is formed, however, on the assumption that the openings at the two surfaces are aligned. As a result, the contact opening 608 at the underside of the substrate 602 exposes an edge of the material filling the via 610 and also a portion of the surface of the underside of the substrate. When a contact is formed in this opening, the via material is connected to the substrate.

The via 612 is formed in accordance with the inventive arrangement, and is formed a of a high aspect ratio part 612a, and a wider part 612b, to provide the T-type structure as discussed above. As can be seen on FIG. 6, as with the via 610 the high aspect ratio opening 612a is formed such that it is not perpendicular to the substrate surface. However the problem caused by this is avoided by the wider portion 612b, which ensures that the opening 606 in the oxide layer 604 exposes only the material in the opening. Thus the provision of a wider opening toward a surface of the substrate ensures that the prior art problem does not arise.

Figure 7:
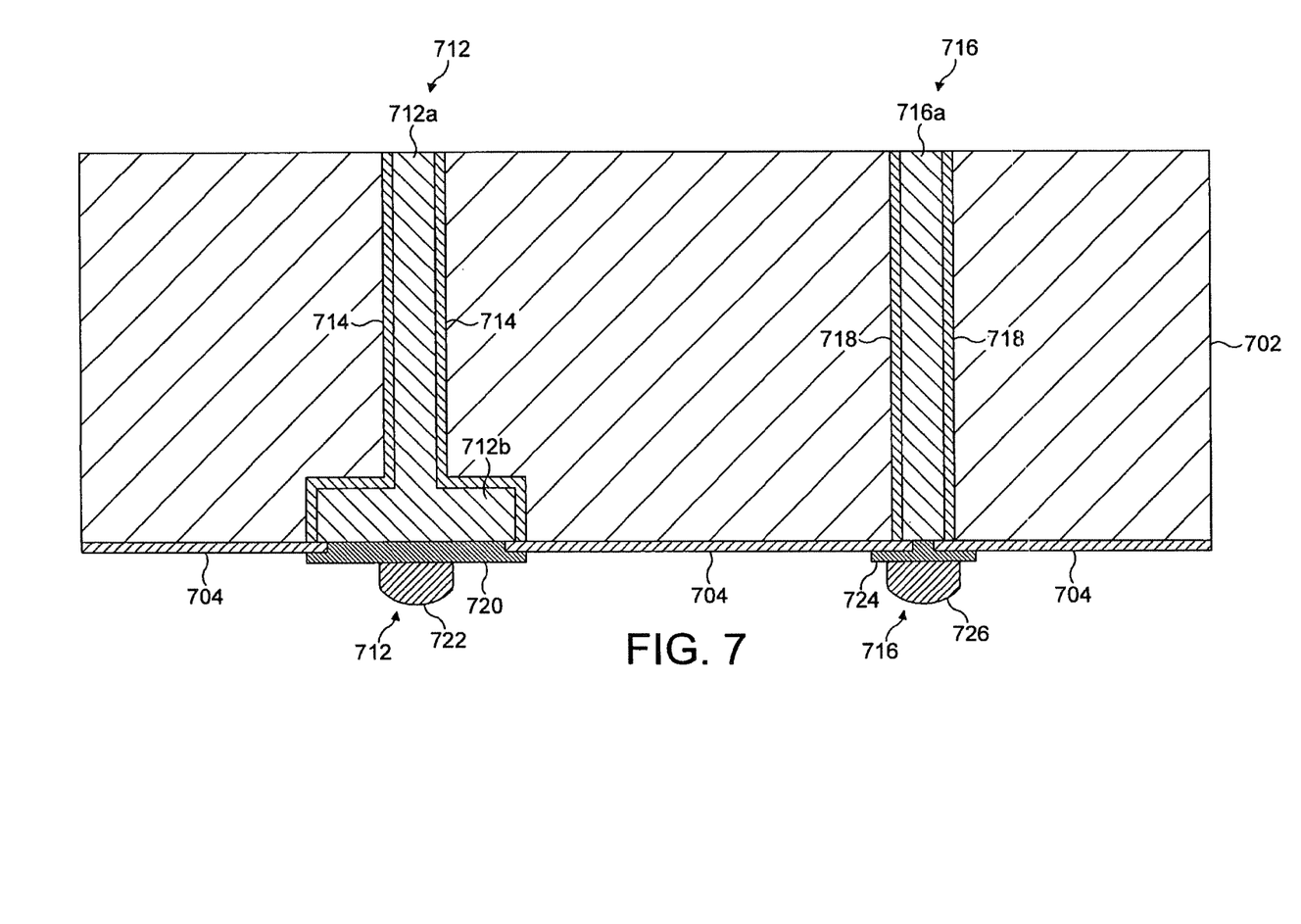
FIG. 7 illustrates an application of an advantageous inventive structure in accordance with an inventive arrangement.

With reference to FIG. 7, a further advantage afforded by this inventive arrangement is described. FIG. 7 shows an exemplary substrate 702. Two vias are formed through the substrate 602, denoted by reference numerals 712 and 716. An oxide layer 704 is formed on the underside of the substrate, having openings for allowing connection to the material formed in the vias 712 and 716.

The via 712 is formed in accordance with the inventive arrangement, and has a high aspect ratio portion, or narrow portion, 712a, and a wider portion 712b. The via is shown formed with silicon dioxide sidewalls providing electrical insulation, denoted by reference numeral 714.

The via 716 is formed in accordance with the prior art, and has a high aspect ratio portion, or narrow portion, 716a. The via is shown formed with silicon dioxide sidewalls providing electrical insulation, denoted by reference numeral 718.

For ease of illustration, the non-perpendicular direction of the via 716 is not shown, but it will be understood that the via will be formed as discussed hereinabove with reference to via 610 of FIG. 6.

Each of the vias 712 and 716 is preferably filled with polysilicon material.

In the formation of gold stub bump contacts for the device, a contact material is formed to contact the via material, and the bump is formed on such contact material. For the prior art via, 716, a gold stub bump 726 is formed over a contact metal 724, the contact metal being formed in the opening through the silicon dioxide to contact the material formed in the via 716. As can be seen in FIG. 7, in the prior art and with current fabrication techniques, the diameter of the gold stub bump is larger than the width of the via 716. As a result, a number of interfaces of different materials are subject to bump forces: with reference to FIG. 7, it can be seen that the silicon substrate 702, polysilicon layer 718, silicon dioxide layer 704 and the contact metal 724 are subject to bump forces. This may cause mechanical damage to the interfaces between the materials.

In contrast, in the inventive arrangement with the wider portion 712b in the via, the diameter of the gold stub bump is smaller than the width of the via. There is no overlap with the silicon dioxide layer 704, or the substrate 702 and the sidewalls 714 at the surface. A gold stub bump 722 may be formed on a relatively thick layer 720 of contact metal 722. The possibility to damage the interface between materials in a bump forming process is thus reduced.

It should be noted that the high aspect ratio openings, i.e. the narrow openings, are generally desirable for the upper surface of the substrate, in the described embodiments, so as to sacrifice as little active area as possible in the upper surface. For this reason, there is a desire to form narrow vias in the device. However wider openings are desirable at the underside of the substrate to address the problems discussed with reference to FIGS. 6 and 7: the mis-alignment of the opening of the via due to non-perpendicular opening; and the need to facilitate more robust contacting. Thus the inverse T-shape structured via is preferably formed in the substrate.

A still further advantage is provided by the inverted T-shape via. Where the field oxide layer on the underside of the substrate is thin, such as layers 604 and 704 in FIGS. 6 and 7, the via structure helps to reduce the capacitance from the bonding pad to the bulk substrate. The bonding pad is formed on the material in the wide-opening of the via. As can be seen, for example in FIGS. 6 and 7, the contact opening is narrow relative to the width of the via at the surface. This increases the distance between the contact pad and the substrate, and hence reduces the capacitance therebetween. The alternative for reducing this capacitance is to form the field oxide layer of a greater thickness. However it is desirable to make the field oxide thin, as this makes forming the contact openings easier. Thus the advantageous via shape described helps to isolate the bonding pad from the bulk substrate better than a direct narrow via structure. The inventive arrangement preferably allows for the thickness of the oxide layer formed on the substrate surface to be reduced.

A further advantage of the described inventive arrangement, in embodiments, is that the wider portion of the via allows for a larger contact opening to be formed than would be possible with only a high aspect ratio opening. This provides a larger contact surface area for contact between a metal contact layer and the conductive material filling the via. This provides for an advantageous contact resistance.

Yet another advantage of the inventive arrangement, in embodiments, is related to robustness of the process. Since there is non uniformity in an etching across the wafer area, in prior art arrangements some of the via holes will be etched through, while others are still only partially etched through. Continuing etching to form all the holes completely through the wafer will result in notching, and other undesirable effects against the back surface, with those vias that were completed first (if etching started from the top surface). With the arrangement where a two-stage etch is used with a narrow opening and a wide opening, these effects become irrelevant. They may still occur, but due to the stepped via structure they have no adverse effect.

Returning to the Figures, the further steps for forming the preferred photo-detector are described, following from FIG. 2(h).

The photo-resist layer 47 is removed from the upper surface of the substrate 30, and a layer of silicon dioxide grown on the wafer as shown in FIG. 2(i). The silicon dioxide is grown on the upper surface of the substrate as illustrated by reference numerals 50a, on the inside of the openings 45 and 49 as illustrated by reference numerals 50b, and on the underside of the substrate as illustrated by reference numerals 50c. The silicon oxide grows fastest on the inner walls of the openings 45 and 49, as represented by growth 50b, and on the underside of the substrate, as represented by growth 50c. The silicon dioxide 50a on the upper surface of the substrate forms a thin layer. The opening through the substrate is thus narrowed as illustrated by FIG. 2(i). The width of the main opening 45 can now be denoted as $x^1$ and the width of the narrower opening 49 can now be denoted as $y^1$.

A layer of polysilicon is then grown on the whole substrate, including the upper surface, the underside surface, and the inner walls of the openings 45 and 48 as shown in FIG. 2(j). As an alternative to polysilicon, any sufficiently conductive material may be grown. The polysilicon is grown such that the openings 45 and 49 are fully filled with polysilicon as denoted by reference numeral 58, and polysilicon layers 56 are formed on the upperside and underside of the substrate.

The polysilicon layer is then grinded/polished in order to remove the polysilicon formed on the upper surface and lower surface of the substrate. Standard lithographic techniques may be used to remove the polysilicon. As a result the structure illustrated in FIG. 2(k) is obtained, where the polysilicon remains only in the openings 45 and 49 as denoted by reference numeral 58.

In further steps not illustrated in the Figures, an oxide layer is then grown over the upper and lower surfaces of the substrate to cover the exposed polysilicon.

Contact openings are then etched in the oxide layer on both sides of the substrate through the silicon dioxide layers as illustrated in FIG. 2(l). On the upperside of the substrate, contact openings 64a are etched through the silicon dioxide layer 50a through to the active area of the photo-diode anode 32. A contact opening 64b is etched to the polysilicon layer 58. On the underside of the substrate, a contact opening 66a is etched through to the polysilicon layer 58, and a contact opening 66b is etched through to the photo-diode cathode 40 (i.e. the bulk connection).

Aluminium layers are then deposited on both sides of the substrate, and patterned using the standard lithographic techniques. The resulting structure is shown in FIG. 2(m). An aluminium layer 68 is formed and patterned over the upper surface of the substrate such that the aluminium layer 68 makes contact through each of the openings 64a and 64b with the polysilicon layer 58 and the active area of the photo-diode anode 32. An aluminium layer 70 is formed and patterned on the underside of the device to make contact through the opening 66a with the polysilicon layer 58. A further aluminium layer 72 is formed and patterned on the underside of the device to make contact through the opening 66b with the active area of the photo-diode cathode 40.

Figure 2:
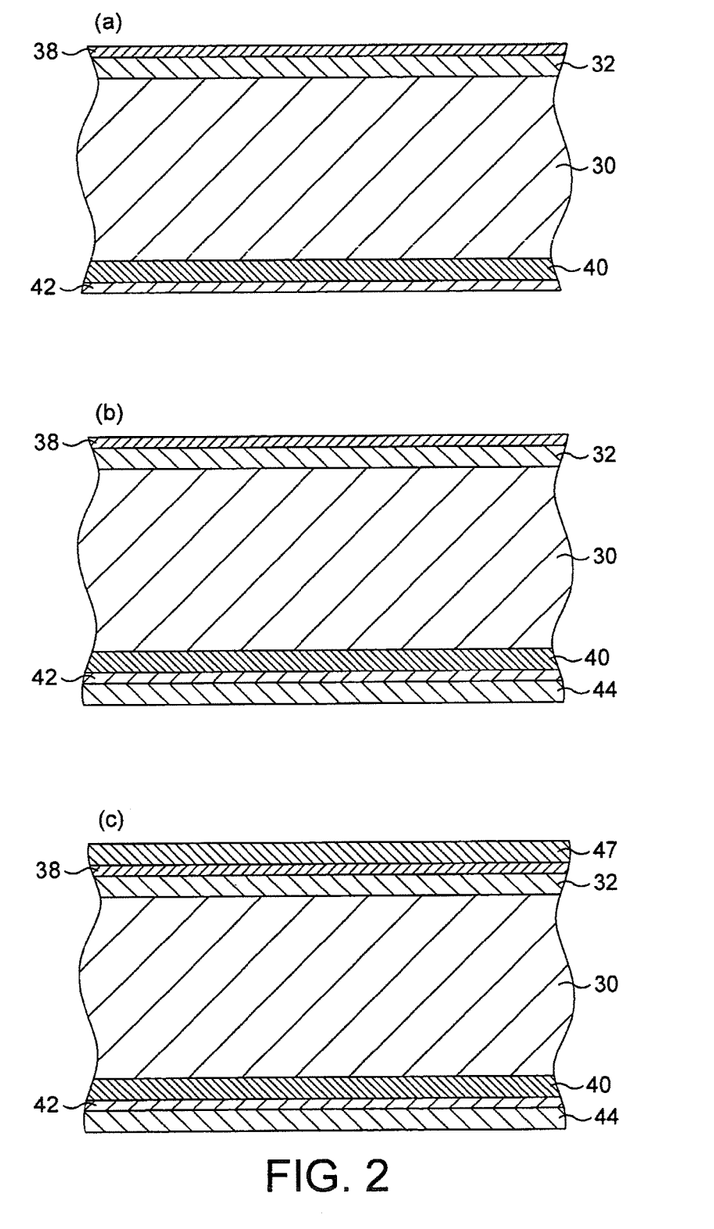
FIGS. 2(a) to 2(n) illustrate the main steps in manufacturing a photodetector device in accordance with a preferred embodiment of the invention.

The structure shown in FIG. 2(*m*) has aluminium contact pads 70 and 72 for both the anode and the cathode on the underside of the substrate.

FIGS. 2(*a*) to 2(*m*) illustrate the formation of, and the structure of, a single photo-diode. For an array of photo-diodes, manufactured on a single silicon chip, a similar structure is provided throughout the whole device. Where an array of photo-diodes are provided on a single silicon chip, a single cathode contact may be common to several or all photo-diodes.

Referring to FIG. 2(*n*), there is shown an upper view of the photo-diode cell of FIG. 2(*m*) viewed from above, i.e. looking down on the device toward the aluminium contact layer 68. The central circle 68 denotes the aluminium contact layer formed over the surface of the polysilicon opening. The square area 32 around the aluminium contact layer 68 denotes the active area of the anode of the photo-diode, which consists of the p+ type region with a layer of silicon dioxide overlaid. The perimeter region 30 denotes the substrate covered by the silicon dioxide layer at the extreme of the active area, where the active area has ceased. The specific shape of the active area and the photo-diode cell may be implementation-dependent, and the arrangement of FIG. 2(*m*) is representative only.

Thus in accordance with the invention and its embodiments the electrical connections for all photo-diodes are provided on the underside of the substrate, for connection off-chip. The electrical connections may be taken off-chip by wire-bonding or bump-bonding, for example, the underside of the substrate to electrical connectors or pads. The inventive arrangement disclosed has a significant advantage in that the contact from the upper surface of the device to the lower surface of the device, such that all electrical contacts may be made at the lower surface of the device, is provided through the device rather than adjacent to the device. As such the overall footprint of the individual photo-diode device (or more generally the photodetector), including the electrical connection from the upper surface to the lower surface, is reduced. Although in the illustrated embodiment the electrical connection from the upper surface of the device to the lower surface of the device is shown to be located in a central position, in accordance with embodiments of the invention the position of this electrical interconnection may be anywhere within the active area of the photo-diode device, i.e. the area 32 denoted by cross hatching in FIG. 2(*n*).

FIGS. 2(*a*) to 2(*n*) illustrate an exemplary process for forming a structure in accordance with the invention. The invention is not limited, however, to such a process. One skilled in the art will appreciate that a structure adhering to the inventive principles may be obtained using an alternative process. In particular, it should be noted that the process described, and the sequence of processes, is exemplary, and the invention is not limited to the processes steps and sequence of process steps set forth herein with respect to described embodiments. The essential features of the described inventive arrangements are set forth by the appended independent claims. Only those features essential to an inventive arrangement as set forth in an appended independent claim are essential to the invention.

For example, in an alternative, the n+ type layer is doped on the under or lower side of the substrate to form the cathode contact layer. The via is then formed through the substrate between the upper and lower surfaces. The p+ type layer is then formed at the upper surface of the substrate, followed by the formation of the conductive material in the via.

One skilled in the art will identify alternative processes for achieving the inventive structure. The processes described herein, and the order in which any process is described as being carried out, are exemplary and non-limiting.

Figure 3:
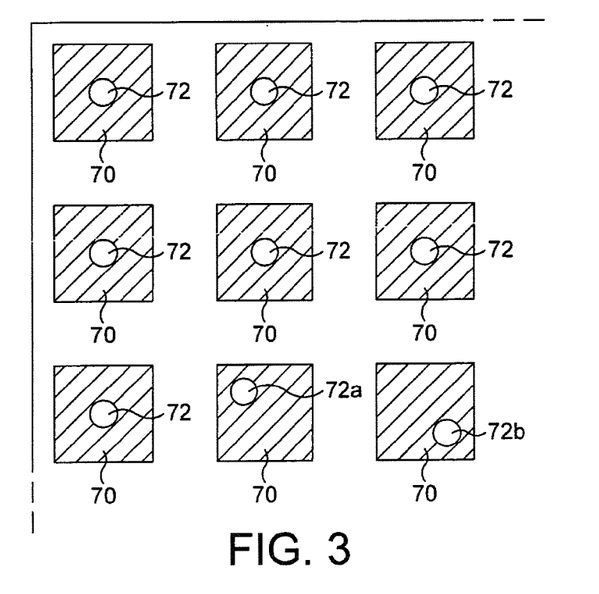
FIG. 3 illustrates a plan view of a photodetector array manufactured in accordance with the process steps of FIGS. 2 to 15.

Referring now to FIG. 3, there is illustrated schematically the structure of an array manufactured according to the techniques of embodiments of the present invention. As can be seen from FIG. 3, generally the substrate or wafer surface is provided with a plurality of active areas 70, corresponding to active areas of photodiodes. Although the active areas are shown to be rectangular, the shape of the active areas is not relevant to the present invention and may vary. Each active area 70 is associated with a via 72, which is formed through the substrate. Although the vias are shown to have a circular cross-section, the shape of the cross-section of the vias is not relevant to the present invention and may vary. FIG. 3 is deliberately simplified to illustrate the described embodiment of the invention. Each of the active areas 70 is conductively connected to its associated conductive via by means not shown, but which will be apparent from FIG. 2(*m*).

It should also be understood that the via need not be formed generally in the middle of the photodiode. The advantages of the invention are achieved by forming the via such that it is within the photodiode rather than adjacent to it or otherwise proximate to it. As illustrated in part of FIG. 3, for example, reference numeral 72a and 72b denote alternative positions within the photodiode device for forming the via.

The present invention thus provides a technique for constructing a photo-detector array which has two significant advantages.

The inventive technique does not require the provision of space at the edge of the array for the connection of the electrical output signals from the array. This advantage is obtained by connecting all signals from the semiconductor devices through the substrate, such that they can be connected on the underside of the array rather than the side of the array.

Figure 4:
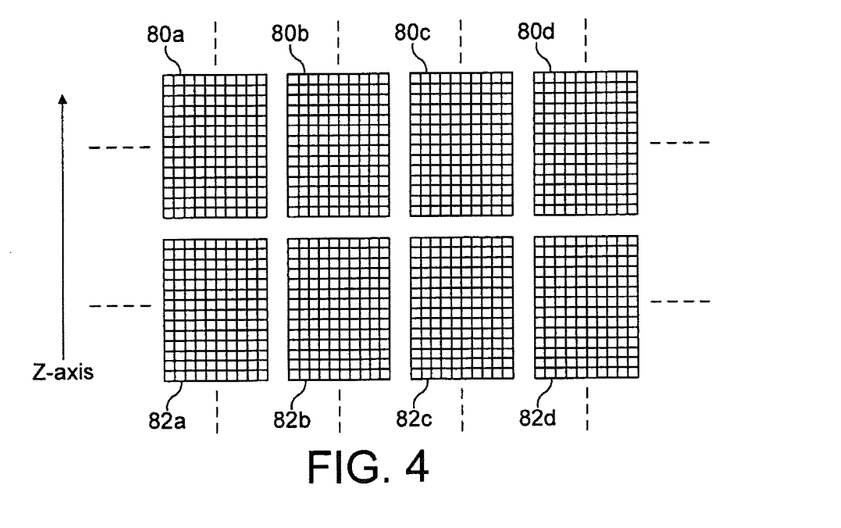
FIG. 4 illustrates the construction of a large photodetector array in accordance with an advantageous implementation of the present invention.

As a result of the removal of the connections from the edge of the array, previously provided in the z direction, there is provided the possibility to extend the size of the overall photo-detector array in the z-axis. Referring to FIG. 4, a set of photo-detector arrays 80a to 80d in accordance with the known techniques for assembling arrays is placed together with a further set of arrays 82a to 82d, such that the overall array is extended in the z-axis. As will be appreciated, the array may be further extended in the z-axis. Although the arrays in FIG. 4 are shown slightly spaced apart, this is only to illustrate the fact that separate arrays are joined in two dimensions. In practice the arrays are in close proximity to each other in both directions, so as to combine to make a larger array. As such, a tiled structure of arrays can be built in two dimensions, to improve the performance of imaging systems.

Figure 5:
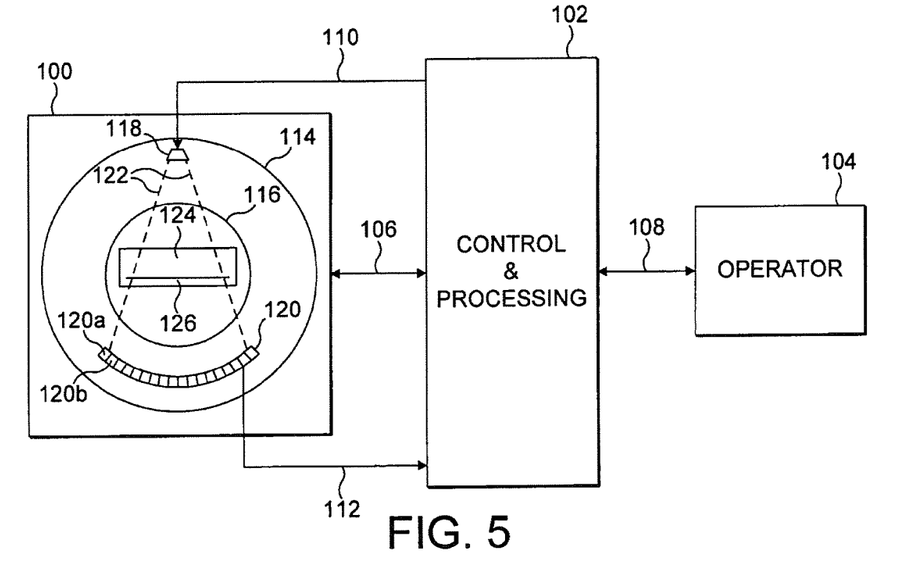
FIG. 5 illustrates a CT imaging system or machine within which the present invention may be advantageously incorporated in an embodiment.

The arrays 80a to 80d and 82a to 82d can be considered as sub-arrays, which together form a photo-detector array. The sub-arrays can be considered to form a matrix which forms a photo-detector array. The matrix effectively extends in two-dimensions, although in practice, as can be seen in FIG. 5 below, the matrix is curved such that the array extends in a third dimension.

The inventive technique further has the advantage that no connections for the photodiode devices are required outside of the substrate area of the devices. This means that the overall area required to implement the photodiode device is not increased, the area required corresponding to the size of the active area of the device itself. This is advantageous particularly in photodiode arrays in which a number of devices are provided, the size of such arrays being reduced using the invention compared with any prior art techniques.

Whilst the present invention has been described in relation to a particular processing technique for forming the advantageous structure of the present invention, it is not limited to such a technique. A chemical or mechanical method may be utilised to manufacture the hole through the substrate, although a chemical method is preferred to maintain structural integrity. Although inductively coupled plasma etching is foreseen as a practical solution to achieve this, other dry etching methods, drilling, spark erosion or laser drilling may also be used.

The invention enables the manufacture of fully 'tileable' detector structures with highly uniform detector properties, which include a dense array of photodiodes compared to the prior art.

The present invention has been described herein by way of reference to specific, non-limiting examples. For example, the invention is more generally applicable than the described application to photo-detectors in imaging systems. In addition, the invention is not limited to any particular material given herein by way of example. The invention is more generally applicable to substrates, wafers and semiconductor devices and the manufacture thereof. The invention, however, is clearly advantageously applicable in implementations requiring arrays of semiconductor devices that must be connected off the device.

Referring to FIG. 5, there is illustrated the main elements of a CT imaging machine within which a photo-detector array may be constructed in accordance with a preferred embodiment of the invention, and advantageously utilised. The construction of such machines is well-known in the art, and will be familiar to one skilled in the art. Only the main elements of such a machine are shown in FIG. 5, to illustrate the use of the present invention.

The machine principally comprises a scanner generally designated by reference numeral 100, a control and processing means generally designated by reference numeral 102, and an operator interface generally designated by reference numeral 104.

The scanner 100 generally comprises a cylindrical structure 114, a cross-section through which is illustrated in FIG. 5. Within the cylindrical structure 114 there is mounted an x-ray source 118 and an array of photo-detectors 120. The array of photo-detectors 120 comprises a plurality of arrays such as the arrays 80 of FIG. 4. Thus the array 120 is made up of a plurality of arrays 120*a*, 120*b* etc. In the arrangement of FIG. 5, the photo-detector arrays 120*a*, 120*b* etc are implemented in a tiled structure, and the arrays are connected not only in the plane shown in the cross-section of FIG. 5, but also in the z-direction, i.e. into the page along the length of the cylindrical structure 114.

The X-ray source 118 emits X-rays under the control of a signal on line 110 from the control and processing means 102. The X-rays, having a radiation pattern in cross-section generally designated by dashed lines 122, have a footprint which falls onto the photo-detector array 120, which in accordance with the desired techniques extends in the direction of the cylindrical axis, as well as in the direction shown in the cross-section of FIG. 5. The outputs from the photo-detectors are provided to the control and processing means 102 on a signal line 112.

An object to be imaged, such as a patient 124, is placed on a table 126 which is typically moved through the imaging machine in the z-direction. In utilising a photo-detector array as described, any movement of the table may be reduced or rendered unnecessary.

The control and processing means 102 includes all necessary means for controlling the mechanical and electronic operation of the scanner 100, including the means for controlling the X-ray source 118 and for processing signals received from the photo-detector array 120. Additional transfer of signals between the control and processing means and the scanner 100 are represented by signal connections 106.

The operator interface 104 communicates with the control and processing means, as represented by signals 108. The operator interface 104 preferably is used to control the operation of the scanner 100, and display results of the scanning process.

FIG. 5 represents one useful application of a photo-detector array constructed in accordance with the principles of a preferred embodiment of the present invention. Other useful and advantageous applications will be apparent to one skilled in the art.

It should be understood that the invention is more generally applicable than the examples given herein. One skilled in the art will understand the broader applicability of the present invention. The scope of the invention is defined by the appended claims.

The invention claimed is:

1. A substrate comprising:
   a plurality of photodetectors;
   a first active area on a first surface of the substrate; and
   a second active area on a second surface of the substrate,
   wherein the plurality of photodetectors are each provided with a conductive via electrically isolated from the substrate, each conductive via extending through its corresponding photodetector from the first surface of the substrate to the second surface of the substrate for connecting the first active area to the second surface of the substrate, and each conductive via being fully and continuously filled with a conductive material, and having no joints;
   each conductive via having: a first portion entirely of a first width extending from the first surface into the substrate by a first depth, the first portion not extending perpendicularly from the first surface such that an extrapolation of the first portion to the second surface does provide an opening of the first width at the second surface which does not align with an opening of the first portion of the first width at the first surface; and a second portion entirely of a second width extending from the second surface into the substrate by a second depth to abut the first portion, wherein the first width is smaller than the second width and the first depth is larger than the second depth;
   an oxide layer formed over the second surface and having openings aligned with the openings of the first portion of the plurality of conductive vias at the first surface, the openings in the oxide layer exposing only the conductive material filling of the second portion at the second surface; and the second surface comprising electrical connections for the first and second active areas.

2. The substrate according to claim 1 wherein the second portion of the second width is formed proximate the second surface and the first portion of the first width extends from the second portion of the second width to the first surface.

3. The substrate according to claim 1 wherein each conductive via extends through the first active area.

4. The substrate according to claim 1 wherein there is provided a further conductive element on the second surface of the substrate connected to each conductive via.

5. The substrate according to claim 4 wherein the further conductive element on the second surface of the substrate is for making an off-chip connection to the first active area via each conductive via.

6. The substrate according to claim 4 wherein the further conductive element is an aluminum contact element.

7. The substrate according to claim 1 wherein the plurality of photodetectors are photodiodes of a medical imaging system.

8. The substrate according to claim 7 wherein the medical imaging system is a computed tomography system.

9. The imaging system according to claim 7 wherein the medical imaging system has an X-ray radiation source.

10. A method of manufacturing photodetector devices comprising:
    forming a first active area of each photodetector device on a first surface of a substrate;
    forming a second active area on a second surface of the substrate;
    forming a plurality of conductive vias electrically isolated from the substrate, each of the plurality of conductive vias extending through its corresponding photodetector device from the first surface of the substrate to the second surface of the substrate, each of the plurality of conductive vias having: a first portion of entirely a first width, the first portion not being formed perpendicular from the first surface such that an extrapolation of the first portion to the second surface does provide an opening of the first width at the second surface that does not align with an opening of the first portion of the first width at the first surface, and extending to abut a second portion of entirely a second width, the second width being greater than the first width and a depth of the first portion being greater than a depth of the second portion;
    fully and continuously filling the plurality of conductive vias with a conductive material, the plurality of conductive vias having no joints;
    forming an oxide layer over the second surface;
    forming openings in the oxide layer aligned with the openings of the first portion of the plurality of conductive vias at the first surface, the openings in the oxide layer exposing only the conductive material filling of the second portion at the second surface; and
    connecting each first active area respectively to each one of the plurality of conductive vias such that the first active area is connected to the second surface of the substrate.

11. The method according to claim 10 further comprising forming the second portion of the second width proximate the second surface and forming the first portion of the first width extending from the second portion of the second width to the first surface.

12. The method according to claim 10 further comprising forming each conductive via extending through the first active area.

13. The method according to claim 10 further comprising the step of providing a further conductive element on the second surface of the substrate connected to the conductive via.

14. The method according to claim 13 wherein the further conductive element on the second surface of the substrate is provided for making an off-chip connection to the first active area via the conductive via.

* * * * *